United States Patent [19]

Krause et al.

[11] Patent Number: 4,871,472
[45] Date of Patent: Oct. 3, 1989

[54] ESTERS IN FERROELECTRIC MIXTURES

[75] Inventors: Joachim Krause, Dieburg; Volker Reiffenrath, Darmstadt; Thomas Geelhaar, Mainz, all of Fed. Rep. of Germany

[73] Assignee: Merck Patent Gesellschaft mit Beschrankter Haftung, Darmstadt, Fed. Rep. of Germany

[21] Appl. No.: 124,789

[22] PCT Filed: Feb. 5, 1987

[86] PCT No.: PCT/EP87/00055

§ 371 Date: Oct. 9, 1987

§ 102(e) Date: Oct. 9, 1987

[87] PCT Pub. No.: WO87/05013

PCT Pub. Date: Aug. 27, 1987

[30] Foreign Application Priority Data

Feb. 13, 1986 [DE] Fed. Rep. of Germany ....... 3604462

[51] Int. Cl.$^4$ .................. G02F 1/13; C09K 19/30; C07C 69/76
[52] U.S. Cl. .................... 252/299.65; 252/299.01; 252/299.63; 252/299.67; 252/299.61; 350/350 R; 350/350 S; 558/268; 558/270; 560/59; 560/73; 560/102; 560/106; 560/107; 560/108; 560/109
[58] Field of Search ............... 252/299.01, 299.63, 252/299.65, 299.67; 350/350 R, 350 S; 560/59, 73, 102, 106, 107, 108, 109; 558/268, 270

[56] References Cited

U.S. PATENT DOCUMENTS

| | | | |
|---|---|---|---|
| 4,110,243 | 8/1978 | Ahnick et al. | 252/299.67 |
| 4,222,888 | 9/1980 | Dubois et al. | 252/299.64 |
| 4,235,736 | 11/1980 | Beguin et al. | 252/299.65 |
| 4,368,135 | 1/1983 | Oeman | 252/299.63 |
| 4,505,838 | 3/1985 | Romer et al. | 252/299.63 |
| 4,526,704 | 7/1985 | Petrzilka et al. | 252/299.63 |
| 4,621,901 | 11/1986 | Petazilka et al. | 252/299.63 |
| 4,622,165 | 11/1986 | Kano et al. | 252/299.01 |
| 4,637,897 | 1/1987 | Kelly | 252/299.63 |
| 4,728,458 | 3/1988 | Higuchi et al. | 252/299.65 |
| 4,737,313 | 4/1985 | Saito et al. | 252/299.63 |
| 4,769,176 | 9/1988 | Bradshaw et al. | 252/499.65 |
| 4,780,242 | 10/1988 | Miyazawa et al. | 252/299.65 |
| 4,808,333 | 2/1989 | Huynh-Ba et al. | 252/299.63 |
| 4,818,432 | 4/1989 | Miyazana et al. | 252/299.01 |

FOREIGN PATENT DOCUMENTS

| | | | |
|---|---|---|---|
| 220747 | 5/1967 | European Pat. Off. | 252/299.01 |
| 188222 | 7/1981 | European Pat. Off. | 252/299.01 |
| 156726 | 10/1985 | European Pat. Off. | 252/299.01 |
| 201341 | 11/1986 | European Pat. Off. | 252/299.01 |
| 231853 | 8/1987 | European Pat. Off. | 252/299.65 |
| 3525015 | 1/1986 | Fed. Rep. of Germany | 252/299.01 |
| 61-197669 | 9/1986 | Japan | 252/299.01 |
| 61-229842 | 10/1986 | Japan | 252/299.01 |
| 61-257948 | 11/1986 | Japan | 252/299.65 |
| 62-22889 | 1/1987 | Japan | 252/299.01 |
| 62-123153 | 6/1987 | Japan | 252/299.65 |
| 62-81239 | 8/1987 | Japan | 252/299.65 |
| 2061311 | 5/1981 | United Kingdom | 252/299.67 |
| 8701717 | 3/1987 | World Int. Prop. O. | 252/299.62 |

OTHER PUBLICATIONS

Decobert G., et al., Mol. Cryst. Liq. Cryst., vol. 114, pp. 237–247 (1984).
Gray G. W. et al., Mol. Cryst. Liq. Cryst., vol. 67, No. 1-4, pp. 1–24 (1981).
Dubois J. C. et al., Mol. Cryst. Liq. Cryst., vol. 42, No. 1-3, pp. 139–152 (1977).
Lepesant J. P. et al., Mol. Cryst. Liq. Cryst., vol. 129, pp. 61–74 (1985).
Coates D., Liquid Crystals, vol. 2, No. 4, pp. 423–428 (1987).

Primary Examiner—Teddy S. Gron
Attorney, Agent, or Firm—Millen, White & Zelano

[57] ABSTRACT

Compounds of the formula I $$R^1+A^1-Z^1\!\!\!\rightarrow_m\!\!-\!\!\langle O \rangle\!\!-\!\!\langle O \rangle\!\!-\!\!\rangle_n\!\!-CO-O+A^2-Z^2\!\!\!\rightarrow_o A^3-R^2 \quad \text{I}$$

with X substituent on ring wherein
$R^1$ and $R^2$ each independently of one another are R, OR, OCOR, COOR or OCOOR,
is alkyl with 1 to 15 C atoms, wherein one or more $CH_2$ groups which are not adjacent and are not linked by O can also be replaced by $-O-$, $-CO-$, $-O-CO-$, $-CO-O-$, $-CH$—halogen, $-CHCN-$ and/or $-CH=CH-$,
$A^1$, $A^2$ and $A^3$ each independently of one another are 1,4-phenylene or trans-1,4-cyclohexylene,
m, n and o are each 0 or 1,
$m+n+o$ is 0, 1 or 2,
$Z^1$ and $Z^2$ each independently of one another are $-CH_2-O-$, $-OCH_2-$, $-CH_2CH_2-$ or a single bond and
X is F, Cl, Br, I or CN,
with the provisos given in claim 1, can be used as components of ferroelectric liquid crystal phases.

2 Claims, No Drawings

ESTERS IN FERROELECTRIC MIXTURES

The invention relates to esters of the formula I

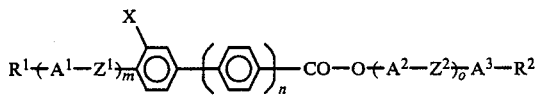

wherein
$R^1$ and $R^2$ each independently of one another are R, OR, OCOR, COOR or OCOOR,
R is alkyl with 1 to 15 C atoms, wherein one or more $CH_2$ groups which are not adjacent and are not linked by O can also be replaced by —O—, —CO—, —O—CO—, —CO—O—, —CH-halogen, —CHCN— and/or —CH=CH—,
$A^1$, $A^2$ and $A^3$ each independently of one another are 1,4-phenylene or trans-1,4-cyclohexylene,
m, n and o are each 0 or 1,
$m+n+o$ is 0, 1 or 2,
$Z^1$ and $Z^2$ each independently of one another are —$CH_2$—O—, —O$CH_2$—, —$CH_2CH_2$— or a single bond and
X is F, Cl, Br, I or CN,
with the proviso that
(a) X is F, Cl or I if $A^2$ and $A^3$ are each 1,4-phenylene, n=m=0, $Z^2$ is —$CH_2CH_2$— or a single bond and $R^2$ is an alkyl group,
(b) in the case where n=m=0, $A^2$=1,4-phenylene, X is F and $Z^2$ is a single bond, $A^3$ is then 1,4-phenylene, and
(c) in the case where m=n=o=0, $R^1$ and/or $R^2$ is OCOR, COOR or OCOOR.

The compounds of the formula I are suitable as components of chiral tilted smectic phases which have ferroelectric properties.

Chiral tilted smectic liquid crystal phases with ferroelectric properties can be prepared by adding a suitable chiral doping substance to base mixtures with one or more tilted smectic phases (L. A. Beresnev et al., Mol. Crystl. Liq. Cryst. 89, 327 (1982); and H. R. Brand et al., J. Physique 44 (lett.), L-771 (1983)). Such phases can be used as dielectrics for rapid-switching displays which, for example, are based on the principle of SSFLC technology described by Clark and Lagerwall (N. A. Clark and S. T. Lagerwall, Appl. Phys. Lett. 36, 899 (1980) and U.S. Pat. No. 4,367,924), on the basis of the ferroelectric properties of the chirally tilted phase. In this phase, the elongated molecules are arranged in layers, the molecules having a tilting angle to the layer perpendicular. On progressing from layer to layer, the tilting direction changes by a small angle in respect to an axis perpendicular to the layers, so that a helical structure is formed. In displays based on the principle of SSFLC technology, the smectic layers are arranged perpendicular to the plates of the cell. The helical arrangement of the tilting directions of the molecules is suppressed by a very small distance between the plates (about 1-2 μm). The longitudinal axes of the molecules are thereby forced to arrange themselves in a plane parallel to the plates of the cell, which means that two distinct tilting orientations are formed. By applying a suitable alternating electrical field, switching backwards and forwards between these two states can be effected in the liquid crystal phase with spontaneous polarization. This switching operation is considerably faster than in conventional twisted cells (TN-LCD's) based on nematic liquid crystals.

A great disadvantage for many applications of the materials currently available with chirally tilted smectic phases (such as, for example, Sc*) is their low chemical, thermal and light stability. Another adverse property of displays based on chirally tilted smectic mixtures currently available is that the spontaneous polarization has values which are too low, so that the switching time properties of the displays are adversely influenced and/or the pitch and tilt of the phases do not meet the requirements of display technology. Moreover, the temperature range of the ferroelectric phases is usually too small and is predominantly at temperatures which are too high.

It has now been found that as components of chiral tilted smectic mixtures, the compounds of the formula I can substantially reduce the disadvantages mentioned. The compounds of the formula I are thus outstandingly suitable as components of chiral tilted smectic liquid crystal phases. In particular, chiral tilted smectic liquid crystal phases which have a particularly high chemical stability and have favourable ferroelectric phase ranges, especially with wide Sc* phase ranges, are very easy to supercool down to temperatures far below 0° C. without crystallization occurring (even phases according to the invention with a melting point above 0° C. can in general be supercooled to far below 0° C.), and have a favourable pitch height and spontaneous polarization values which are high for such phases, can be prepared with the aid of these compounds. P is the spontaneous polarization in nC/cm$^2$.

The compounds of the formula I have a wide field of use. Depending on the choice of the substituents, these compounds can be used as base materials from which liquid crystal smectic phases are predominantly composed; however, it is also possible for compounds of the formula I to be added to liquid crystal base materials of other classes of compounds, for example in order to vary the dielectric and/or optical anisotropy and/or the viscosity and/or the spontaneous polarization and/or the phase ranges and/or the tilting angle and/or the pitch of such a dielectric.

The invention thus relates to the compounds of the formula I. The invention also relates to the compounds of the formula I for use in ferroelectric liquid crystal mixtures. The invention furthermore relates to ferroelectric liquid crystal phases containing at least one compound of the formula I and liquid crystal display elements, in particular electrooptical display elements, containing such phases.

For simplicity, in the following text Cy is a 1,4-cyclohexylene group, Phe is a 1,4-phenylene group and PheX is a 3-X-1,4-phenylene group.

The compounds of the formula I include those compounds of the part formulae Ia to Ie (with three rings):

| | |
|---|---|
| $R^1$—PheX—COO—$A^2$—$A^3$—$R^2$ | Ia |
| $R^1$—PheX—COO—$A^2$—$Z^2$—$A^3$—$R^2$ | Ib |
| $R^1$—PheX—Phe—COO—$A^3$—$R^2$ | Ic |
| $R^1$—$A^1$—PheX—COO—$A^3$—$R^2$ | Id |
| $R^1$—$A^1$—$Z^1$—PheX—COO—$A^3$—$R^2$ | Ie | and If to Im (with four rings):

$R^1—A^1—PheX—COO—A^2—A^3—R^2$　　If $R^1—A^1—Z^1—PheX—COO—A^2—A^3—R^2$　　Ig $R^1—A^1—Z^1—PheX—COO—A^2—Z^2—A^3—R^2$　　Ih $R^1—A^1—PheX—COO—A^2—Z^2—A^3 R^2$　　Ii $R^1—PheX—Phe—COO—A^2—A^3—R^2$　　Ij $R^1—PheX—Phe—COO—A^2—Z^2—A^3—R^2$　　Ik $R^1—A^1—PheX—Phe—COO—A^3—R^2$　　Il $R^1—A^1—Z^1—PheX—Phe—COO—A^3—R^2$　　Im and In (with two rings):

$R^1—PheX—COO—A^3—R^2$　　In.

Amongst these, those of the part formula Ia, Ib, Ic, id, If and Ij are preferred.

The preferred compounds of part formula Ia include those of the part formulae Iaa to Iad:

$R^1—PheX—COO—Phe—Phe—R^2$　　Iaa $R^1—PheX—COO—Cy—Cy—R^2$　　Iab $R^1—PheX—COO—Phe—Cy—R^2$　　Iac $R^1—PheX—COO—Cy—Phe—R^2$　　Iad

Amongst these, those of the part formulae Iaa and Iab are particularly preferred.

The preferred compounds of the part formula Ib include those of the part formulae Iba to Ibd:

$R^1—PheX—COO—Phe—Z^2—Phe—R^2$　　Iba $R^1—PheX—COO—Cy—Z^2—CY—R^2$　　Ibb $R^1—PheX—COO—Phe—Z^2—Cy—R^2$　　Ibc $R^1—PheX—COO—Cy—Z^2—Phe—R^2$　　Ibd

Amongst these, those of the part formulae Iba and Ibb are particularly preferred.

The preferred compounds of the part formula Ic include those of the part formulae Ica and Icb:

$R^1—PheX—Phe—COO—Phe—R^2$　　Ica $R^1—PheX—Phe—COO—CY—R^2$　　Icb.

The preferred compounds of the part formula Id include those of the part formulae Ida to Idd:

$R^1—Phe—PheX—COO—Phe—R^2$　　Ida $R^1—Cy—PheX—COO—Phe—R^2$　　Idb $R^1—Cy—PheX—COO—Cy—R^2$　　Idc $R^1—Phe—PheX—COO—Cy—R^2$　　Idd.

The preferred compounds of the part formula Ie include those of the part formulae Iea to Ied:

$R^1—Phe—Z^1—PheX—COO—Phe—R^2$　　Iea $R^1—Cy—Z^1—PheX—COO—Phe—R^2$　　Ieb $R^1—Cy—Z^1—PheX—COO—Cy—R^2$　　Iec $R^1—Phe—Z^1—PheX—COO—Cy—R^2$　　Ied.

The preferred compounds of the part formula If include those of the part formulae Ifa to Ifd:

$R^1—Phe—PheX—COO—Phe—Phe—R^2$　　Ifa $R^1—Cy—PheX—COO—Phe—Phe—R^2$　　Ifb $R^1—Cy—PheX—COO—Cy—Cy—R^2$　　Ifc $R^1—Phe—PheX—COO—Phe—Cy—R^2$　　Ifd.

The preferred compounds of the part formula Ig include those of the part formulae Iga to Igd:

$R^1—Phe—Z^1—PheX—COO—Phe—Phe—R^2$　　Iga $R^1—Cy—Z^1—PheX—COO—Phe—Phe—R^2$　　Igb

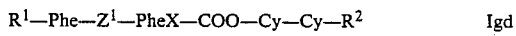　　Igc $R^1—Phe—Z^1—PheX—COO—Cy—Cy—R^2$　　Igd include those of the part formulae Iha to Ihd:

$R^1—Phe—Z^1—PheX—COO—Phe—Z^2—Phe—R^2$　　Iha $R^1—Cy—Z^1—PheX—COO—Phe—Z^2—Phe—R^2$　　Ihb

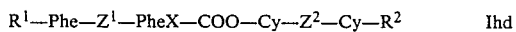Ihc $R^1—Phe—Z^1—PheX—COO—Phe—Z^2—Cy—R^2$　　Ihd

The preferred compounds of the part formula Ii include those of the part formulae Iia to Iid:

$R^1—Phe—PheX—COO—Phe—Z^2—Phe—R^2$　　Iia $R^1—Cy—PheX—COO—Phe—Z^2—Phe—R^2$　　Iib $R^1—Cy—PheX—COO—Phe—Z^2—Cy—R^2$　　Iic $R^1—Phe—PheX—COO—Cy—Z^2—Cy—R^2$　　Iid

The preferred compounds of the part formula Ij include those of the part formulae Ija to Ijd:

$R^1—PheX—Phe—COO—Phe—Phe—R^2$　　Ija $R^1—PheX—Phe—COO—Phe—Cy—R^2$　　Ijb $R^1—PheX—Phe—COO—Cy—Cy—R^2$　　Ijc $R^1—PheX—Phe—COO—Cy—Phe—R^2$　　Ijd

The preferred compounds of the part formula Ik include those of the part formulae Ika to Ikd:

$R^1—PheX—Phe—COO—Phe—Z^2—Phe—R^2$　　Ika $R^1—PheX—Phe—COO—Phe—Z^2—Cy—R^2$　　Ikb $R^1—PheX—Phe—COO—Cy—Z^2—Cy—R^2$　　Ikc $R^1—PheX—Phe—COO—Cy—Z^2—Phe—R^2$　　Ikd

The preferred compounds of the part formula Il include those of the part formulae Ila to Ild:

$R^1—Phe—PheX—Phe—COO—Phe—R^2$　　Ila $R^1—Cy—PheX—Phe—COO—Cy—R^2$　　Ilb

R¹—Cy—PheX—Phe—COO—Phe—R²    IIc

R¹—Phe—PheX—Phe—COO—Cy—R²    IId.

The preferred compounds of the part formula Im include those of the part formulae Ima to Imd:

R¹—Cy—Z¹—PheX—Phe—COO—Phe—R²    Ima

R¹—Phe—Z¹—PheX—Phe—COO—Phe—R²    Imb

R¹—Cy—Z¹—PheX—Phe—COO—Cy—R²    Imc

R¹—Phe—Z¹—PheX—Phe—COO—Cy—R²    Imd.

The preferred compounds of the part formula In include those of the part formulae Ina and Inb:

R¹—PheX—COO—Phe—R²    Ina

R¹—PheX—COO—Cy—R²    Inb.

In the compounds of the formulae above and below, $R^1$ and $R^2$ are preferably R or OR, or furthermore OCOR, COOR or OCOOR. R here is preferably alkyl, or oxaalkyl. Compounds of the formula I wherein one of the radicals $R^1$ and $R^2$ is R or OR and the other radical is OR, OCOR, COOR or —OCOOR are particularly preferred.

R in OCOR or COOR is preferably an alkyl group, which can also be branched, in which one $CH_2$ group is replaced by —CH—halogen—. Halogen is preferably fluorine or particularly preferably chlorine.

If $m=n=o=0$, $R^1$ and/or $R^2$ is OCOR, COOR or OCOOR.

$Z^1$ and $Z^2$ independently of one another are —CH$_2$O—, —OCH$_2$—, —CH$_2$CH$_2$— or a single bond, preferably a single bond.

m, n and o are each 0 or 1, and $m+n+o$ is 0, 1 or 2. Preferably $m=0$ and $n+o=1$.

X is preferably F, Cl or CN, or furthermore Br or I, and fluorine is particularly preferred.

X is F, Cl or I, preferably F, if m and $n=0$, $A^2$ and $A^3$ are each 1,4-phenylene, $Z^2$ is —CH$_2$CH$_2$— or a single bond and $R^2$ is an alkyl group.

$A^3$ is a 1,4-phenylene group if $n=m=0$, $A^2$ is a 1,4-phenylene group, $X=F$ and $Z^2$ is a single bond.

Halogen is preferably F or Cl.

The alkyl radicals R in the groups $R^1$ and/or $R^2$ can be straight-chain or branched. Preferably, they are straight-chain and have 5, 6, 7, 8, 9, 10, 11 or 12 C atoms, and accordingly are preferably pentyl, hexyl, heptyl, octyl, nonyl, decyl, undecyl or dodecyl, and furthermore also methyl, ethyl, propyl, butyl, tridecyl, tetradecyl or pentadecyl.

$R^1$ and $R^2$ together preferably have 12–20 C atoms, in particular 12–16 C atoms.

If R is an alkyl radical in which one ("alkoxy" or "oxaalkyl") or two ("alkoxyalkoxy" or "dioxaalkyl") $CH_2$ groups are replaced by O atoms, it can be straight-chain or branched. Preferably, it is straight-chain and has 5, 6, 7, 8, 9, 10, 11 or 12 C atoms, and accordingly is preferably pentoxy, hexoxy, heptoxy, octoxy, nonoxy, decoxy, undecoxy, dodecoxy, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl, 1,4-dioxaoctyl, 1,4,7-trioxaoctyl, 1,4-dioxanonyl, 1,4-dioxadecyl, or furthermore tridecoxy, tetradecoxy, pentadecoxy, methoxy, ethoxy, propoxy or butoxy.

Compounds of the formula I and of the part formulae above and below with branched side-chain groups $R^1$ or $R^2$ may occasionally be of importance because of a better solubility in the usual liquid crystal base materials, but in particular as chiral doping substances for chirally tilted smectic phases, if they are optically active. However, such compounds are also suitable as components of nematic liquid crystal phases, in particular for avoiding reverse twist. Branched groups of this type as a rule contain not more than one chain branching. Preferred branched radicals are isopropyl, 2-butyl (=1-methylpropyl), isobutyl (=2-methylpropyl), 2-methylbutyl, isopentyl (=3-methyl-butyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 2-octyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 6-methyloctoxy, 6-methyloctanoyloxy, 5-methylheptoyloxycarbonyl, 2-methylbutyryloxy, 3-methylvaleryloxy or 4-methylhexanoyloxy.

The branched side-chain groups $R^1$ or $R^2$ can be an optically active organic radical with an asymmetric carbon atom. The asymmetric carbon atom is preferably linked to two differently substituted C atoms, an H atom and a substituent selected from the group comprising halogen (in particular S, Cl or Br), alkyl and alkoxy with in each case 1 to 5 C atoms and CN. The optically active organic radical R* preferably has the formula

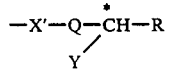

wherein

X' is —CO—O—, —O—CO—, —O—CO—O—, —CO—, —O—, —S—, —CH=CH—, —CH=CH—COO— or a single bond, Q is alkylene with 1 to 5 C atoms, wherein a $CH_2$ group which is not linked to X can also be replaced by —O—, —CO—, —O—CO—, —CO—O— or —CH=CH—, or a single bond, Y is CN, halogen, methyl or methoxy and R is an alkyl group other than Y with 1 to 18 C atoms, wherein one or two non-adjacent $CH_2$ groups can also be replaced by —O—, —CO—, —O—CO—, —CO—O— and/or —CH=CH—.

X' is preferably —CO—O—, —O—CO—, —CH=CH—COO— (trans) or a single bond. —CO—O— and —O—CO— are particularly preferred.

Q is preferably —CH$_2$—, —CH$_2$CH$_2$— or a single bond, particularly preferably a single bond.

Y is preferably CH$_3$, —CN or Cl, particularly preferably —CN.

R is preferably straight-chain alkyl with 1 to 10, in particular 1 to 7, C atoms.

A particularly preferred group of compounds of the formula I comprises those in which the side-chain groups $R^1$ and $R^2$ are straight-chain.

A preferred group of compounds of the formula I comprises the compounds in which the laterally substituted ring is in the outside position, and m is then 0.

Compounds which are 3-nuclear and at the same time the laterally substituted ring in the outside position are therefore particularly preferred.

If compounds of the formula I are optically active, those which contain the group —OCOR, wherein R is an alkyl group which is preferably branched, as $R^1$ or $R^2$ and in which one $CH_2$ group is replaced by —CH—halogen—, halogen preferably being chlorine, or by —CHCN— are particularly preferred. Especially preferred radicals here are $OCOCH(Cl)$—$CH(CH_3)_2$, (2-chloro-3-methylbutyryloxy), —$OCOCH(Cl)$—$CH(CH_3)$—$C_2H_5$, (2-chloro-3-methylvaleryloxy) or —$OCOCH(Cl)$—$CH_2$—$CH(CH_3)_2$ (2-chloro-4-methylvaleryloxy).

The other radical $R^1$ or $R^2$ is then preferably R or OR.

In optically active compounds of the formula I which contain the asymmetric C atom in the group —OCOR*, the lateral substituent on the ring is preferably fluorine or chlorine. These compounds are preferably 2- or 3-nuclear.

Amongst the compounds of the formula I and of the part formulae above and below, those in which at least one of the radicals contained therein has one of the preferred meanings mentioned are preferred. Particularly preferred smaller groups of compounds are those of the formula I1 to I37:

| | |
|---|---|
| RO—PheCl—COO—Phe—Phe—R | I1 |
| RO—PheF—COO—Phe—Phe—R | I2 |
| R—PheX—COO—Phe—Phe—OR | I3 |
| RO—PheX—COO—Phe—Phe—OR | I4 |
| RO—PheX—COO—Phe—Cy—Cy—R | I5 |
| RO—PheCl—COO—Phe—Cy—R | I6 |
| R—PheCN—COO—Phe—Cy—R | I7 |
| RO—Phe—OCH$_2$—PheX—COO—Phe—Phe—R | I8 |
| R—Phe—CH$_2$CH$_2$—PheX—COO—Phe—Phe—R | I9 |
| R—Phe—CH$_2$O—PheX—COO—Cy—Cy—R | I10 |
| R—PheX—COO—Phe—CH$_2$O—Phe—R | I11 |
| RO—Phe—PheX—COO—Phe—Phe—R | I12 |
| RO—Phe—PheX—COO—Cy—CY—R | I13 |
| R—Phe—PheX—COO—Phe—Phe—OR | I14 |
| RO—Phe—PheX—COO—Phe—Phe—OR | I15 |
| R—Cy—PheX—COO—Phe—Phe—R | I16 |
| R—PheX—COO—Cy—CH$_2$CH$_2$—Phe-OR | I17 |
| R—PheX—Phe—COO—Phe—OR | I18 |
| R—PheX—Phe—COO—Cy—R | I19 |
| RO—Phe—PheX—COO—Phe—R | I20 |
| RO—Phe—PheX—COO—Cy—R | I21 |
| R—PheX—Phe—COO—Phe—Phe—OR | I22 |
| RO—Phe—PheX—Phe—COO—Cy—R | I23 |
| RO—PheF—COO—Phe—CH$_2$CH$_2$—Phe—R | I24 |
| RO—Phe—PheX—COO—Phe—Cy—R | I25 |
| R—Cy—PheX—COO—Cy—Phe—OR | I26 |
| R—Phe—PheX—COO—Phe—CH$_2$CH$_2$—Phe—R | I27 |
| RO—PheCl—COO—Phe—Phe—OCOCH*—Alkyl<br>                                                        \|<br>                                                        Halogen | I28 |
| Alkyl-CH*COO—PheX—COO—Phe—R<br>       \|<br>       Halogen | I29 |
| $(CH_3)_2CH$—CH*—COO—PheX—COO—Phe—R<br>                    \|<br>                    Cl | I30 |
| R—PheX—COO—Phe—Phe—OCOCH*—Alkyl<br>                                       \|<br>                                      Halogen | I31 |
| RCOO—PheX—COO—Phe—Phe—$R^{2*}$ | I32 |
| R—PheX—COO—Phe—Phe—$R^{2*}$ | I33 |
| R—PheX—Phe—COO—Phe—$R^{2*}$ | I34 |
| RO—PheX—Phe—COO—Phe—$R^{2*}$ | I35 |
| RO—PheX—COO—Phe—$R^{2*}$ | I36 |
| RO—PheX—COO—Phe—Phe—$R^{2*}$ | I37. |

$R^{2*}$ here is an optically active organic radical as described for $R^1$ and $R^2$.

X and R here have the abovementioned preferred meanings.

Compounds of the formula I which contain no $S_c$ phases, in particular optically active compounds of the formula I, are likewise suitable as components of ferroelectric liquid crystal phases according to the invention. Optically active compounds of the formula I are also suitable as components of nematic liquid crystal phases, for example for avoiding reverse twist.

All the compounds of the formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. It is thereby also possible to utilize variants which are known per se and are not mentioned here in more detail.

If desired, the starting substances can also be formed in situ, such that they are not isolated from the reaction mixture but are immediately reacted further to give the compounds of the formula I.

The compounds of the formula I can thus be prepared by reducing a compound which otherwise corresponds to the formula I but contains one or more reducible groups and/or C—C bonds instead of H atoms.

Preferred possible reducible groups are carbonyl groups, in particular keto groups, and furthermore, for example, free or esterified hydroxyl groups or aromatically bonded halogen atoms.

The reduction is carried out under conditions under which any CN group present remains intact, preferably by catalytic hydrogenation at temperatures between 0° and about 100° and pressures between 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Preferably suitable catalysts are noble metals such as Pt or Pd, which can be used in the form of oxides (for example $PtO_2$ or PdO), on a support (for example Pd on charcoaL, calcium or strontium carbonate) or in finely divided form.

The compounds of the formula I can also be prepared, for example, by esterification of a corresponding carboxylic acid or of one of its reactive derivatives with a corresponding alcohol or phenol or one of its reactive derivatives.

Particularly suitable reactive derivatives of the carboxylic acids mentioned are the acid halides, above all the chlorides and bromides, and furthermore anhydrides, azides or esters, in particular alkyl esters with 1-4 C atoms in the alkyl group.

Possible reactive derivatives of the alcohols or phenols mentioned are, in particular, the corresponding metal alcoholates or phenolates, wherein the metal is preferably an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane. Water-immiscible solvents can simultaneously advantageously be used for azeotropic removal by distillation of the water formed in the esterification. An excess of an organic base, for example pyridine, quinoline or triethylamine, may occasionally also be used as the solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are as a rule complete after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is to react an acid anhydride or, in particular, an acid chloride with an alcohol, preferably in a basic medium, bases which are of particular importance being alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises a procedure in which the alcohol or the phenol is first converted into the sodium alcoholate or phenolate or potassium alcoholate or phenolate, for example by treatment with ethanolic sodium hydroxide solution or potassium hydroxide solution, this alcoholate or phenolate is isolated and suspended in acetone or diethyl ether together with sodium bicarbonate or potassium carbonate, with stirring, and a solution of the acid chlorine or anhydride in diethyl ether, acetone or DMF is added to the suspension, preferably at temperatures between about $-25°$ and $+20°$.

The phases according to the invention preferably contain at least three, in particular at least five, compounds of the formula I. Chirally tilted smectic liquid crystal phases according to the invention in which the achiral base mixture contains, in addition to compounds of the formula I, at least one other component with negative or relatively low positive dielectric anisotropy are particularly preferred. This/these other component(s) of the achiral base can make up 1 to 50%, preferably 10 to 25%, of the base mixture. Other components with a relatively low positive or negative dielectric anisotropy which are suitable are compounds of the part formulae IIIa to IIIp:

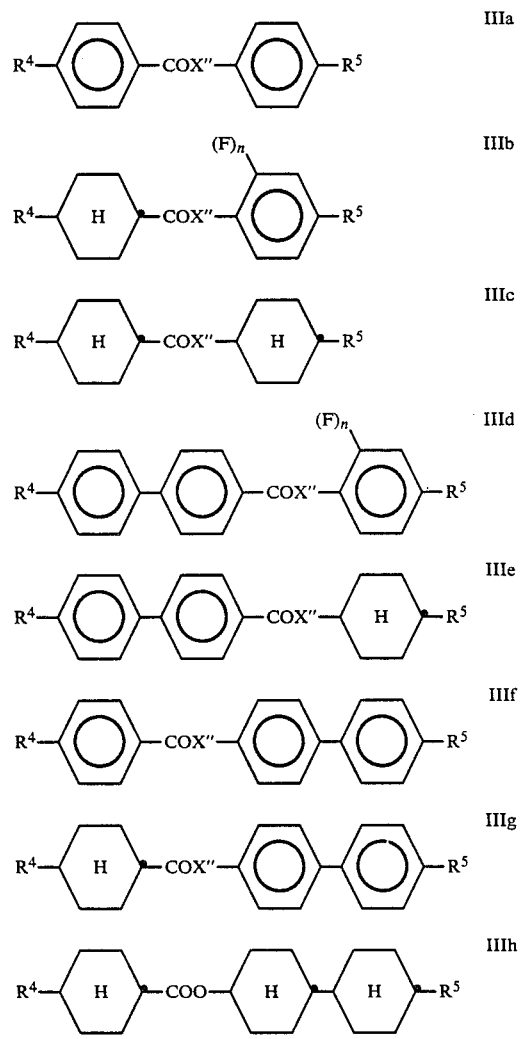

-continued

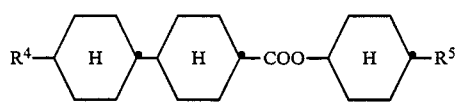  IIIi

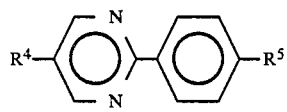  IIIj

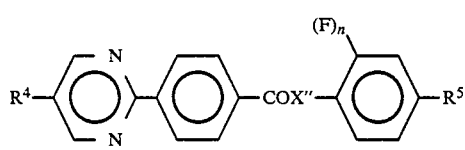  IIIk

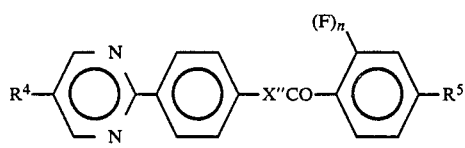  IIIl

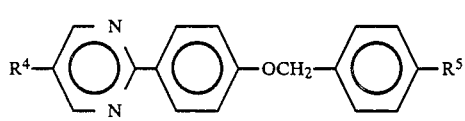  IIIm

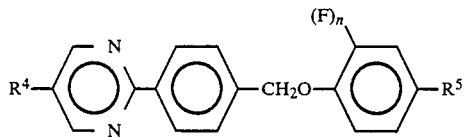  IIIn

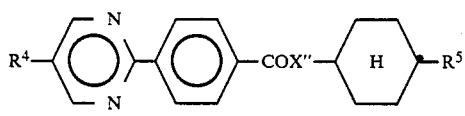  IIIo

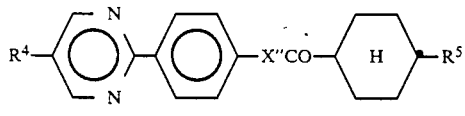  IIIp $R^4$ and $R^5$ are each preferably straight-chain alkyl, alkoxy, alkanoyloxy or alkoxycarbonyl with in each case 3 to 12 C atoms. X" is O or S, preferably O. n is 0 or 1.

The compounds of the part formulae IIIa, IIIb, IIId and IIIf wherein $R^4$ and $R^5$ are each preferably straight-chain alkyl or alkoxy with in each case 5 to 10 C atoms are particularly preferred.

The compounds of the part formulae IIIc, IIIh and IIIi are suitable as additives for lowering the melting point and are usually added to the base mixtures in amounts of not more than 5%, preferably 1 to 3%. $R^4$ and $R^5$ in the compounds of the part formulae IIIc, IIIh and IIIi are preferably straight-chain alkyl with 2 to 7, preferably 3 to 5, C atoms. Another class of compounds which is suitable for lowering the melting point in the phases according to the invention is that of the formula

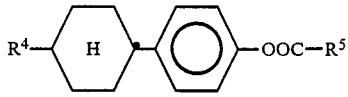  IIIi wherein $R^4$ and $R^5$ have the meaning given as preferred for IIIc, IIIh and IIIi.

Other components with negative dielectric anisotropy which are furthermore suitable are compounds containing the structural element A, B or C.

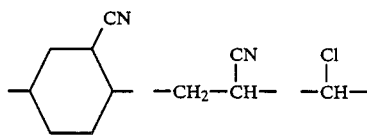

A  B  C

Preferred compounds of this type correspond to the formulae IVa, IVb and IVc:

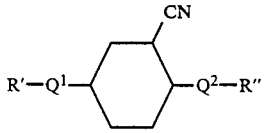  IVa

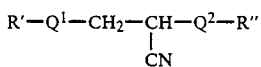  IVb $$R'-Q^3-Q^4-R''' \quad \text{IVc}$$

$R'$ and $R^{41}$ *are each preferably straight-chain alkyl or alkoxy groups with in each case* 2 to 10 C atoms. $Q^1$ and $Q^2$ are each 1,4-phenylene, trans-1,4-cyclohexylene, 4,4'-biphenylyl, 4-(trans-4-cyclohexyl)-phenyl or trans,trans-4,4'-bicyclohexyl, or one of the groups $Q^1$ and $Q^2$ is also a single bond.

$Q^3$ and $Q^4$ are each 1,4-phenylene, 4,4'-biphenylyl or trans-1,4-cyclohexylene. One of the groups $Q^3$ and $Q^4$ can also be 1,4-phenylene, wherein at least one CH group is replaced by N. $R'''$ is an optically active radical with an asymmetric carbon atoms of the structure

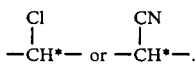

Particularly preferred compounds of the formula IVc are those of the formula IVc':

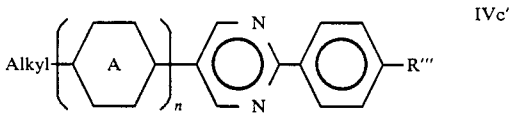  IVc' wherein A is 1,4-phenylene or trans-1,4-cyclohexylene and n is 0 or 1.

Compounds of the formula I are also suitable as components of nematic liquid crystal phases. These liquid crystal phases according to the invention consist of 2 to 15, preferably 3 to 12, components, at least one of which is a compound of the formula I. The other constituents are preferably selected from the nematic or nematogenic substances, in particular the known substances from the classes of azoxybenzenes, benzylideneanilines, biphenyls, terphenyls, phenyl or cyclohexyl benzoates, phenyl or cyclohexylcyclohexanecarboxylates, phenylcyclohexanes, cyclohexylbiphenyls, cyclohexylcyclohexanes, cyclohexylnaphthalenes, 1,3-bis(cyclohexylbenzenes, 4,4'-bis-cyclohexylbiphenyls, phenyl- or cyclohexylpyrimidines, phenyl- or cyclohexyldioxanes, phenyl- or cyclohexyl-1,3-dithianes, 1-phenyl-2-cyclohexylethanes, optionally halogenated stilbenes, benzylphenyl ethers, tolanes and substituted cinnamic acids.

The most important compounds which are suitable as constituents of such liquid crystal phases can be characterized by the formula V $$R^6-L-G-E-R^7 \qquad V$$

wherein L and E are each a carbo- or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| | |
|---|---|
| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine, or CN and $R^6$ and $R^7$ are alkyl, alkoxy, alkanoyloxy or alkoxycarbonyloxy with up to 18, preferably up to 8, carbon atoms, or one of these radicals is also CN, NC, NO$_2$, CH$_3$, F, Cl or Br.

In most of these compounds, $R^6$ and $R^7$ differ from one another, one of these radicals usually being an alkyl or alkoxy group. However, other variants of the envisaged substituents are also customary. Many such substances or mixtures thereof are commercially available. All of these substances can be prepared by methods which are known from the literature.

The phases according to the invention contain about 0.1 to 99, preferably 10 to 95% of one or more compounds of the formula I.

Dielectrics according to the invention containing 0.1 to 40, preferably 0.5 to 30% of one or more compounds of the formula I are furthermore preferred.

The dielectrics according to the invention are prepared in a manner which is customary per se. As a rule, the components are dissolved in one another, preferably at elevated temperature.

The liquid crystal dielectrics according to the invention can be modified by suitable additives so that they can be used in all the types of liquid crystal display elements which have been disclosed to date.

Such additives are known to the expert and are described in detail in the literature. For example, it is possible to add conductive salts, preferably ethyl-dimethyldodecyl-ammonium 4-hexyloxybenzoate, tetrabutylammonium tetraphenylboronate or complex salts of crown ethers (compare, for example, B. I. Haller et al., Mol. Cryst. Liq. Cryst. volume 24, pages 249–258 (1973)) for improving the conductivity, dichroic dyestuffs for the production of coloured guest-host systems or substances for modifying the dielectric anisotropy, the viscosity and/or the orientation of the nematic phases. Such substances are described, for example, in German Offenlegungsschriften 2,209,127, 2,240,854, 2,321,632, 2,338,281, 2,450,088, 2,637,430, 2,853,728 and 2,902,177.

The following examples are intended to illustrate the invention without limiting it. M.p.=melting point, c.p.=clear point. Percentage data above and below are percentages by weight; all the temperature data are given in degrees Celsius. The symbols furthermore have the following meanings: C: crystalline-solid state, S: smectic phase (the index characterizes the phase type), N: nematic state, Ch: cholesteric phase, I: isotropic phase. The number between two symbols indicates the transition temperature in degrees Celsius.

EXAMPLE 1

27.3 g of 3-fluoro-4-n-heptyloxybenzoyl chloride are added to a mixture of 24.0 g of 4'-n-pentyl-hydroxybiphenyl, 7.9 g of pyridine and 150 ml of toluene at 100° C., with stirring, and the reaction mixture is kept at this temperature for a further 6 hours.

After the hydrochloride has been filtered off with suction, the filtrate has been evaporated and the residue has been recrystallized, 4-(3-fluoro-4-n-heptyloxybenzoyloxy)-4'-n-pentylbiphenyl, C 117° Sc 132° N 172° I is obtained.

The following compounds are prepared analogously:
4-(3-fluoro-4-pentyloxybenzoyloxy)-4'-pentylbiphenyl
4-(3-fluoro-4-hexyloxybenzoyloxy)-4'-pentylbiphenyl
4-(3-fluoro-4-heptyloxybenzoyloxy)-4'-pentylbiphenyl
4-(3-fluoro-4-octyloxybenzoyloxy)-4'-pentylbiphenyl
4-(3-fluoro-4-nonyloxybenzoyloxy)-4'-pentylbiphenyl
4-[3-fluoro-4-(1-methylheptoxy)benzoyloxy]-4'-pentylbiphenyl (optically active)
4-[3-fluoro-4-(2-octyloxy)benzoyloxy]-4'-heptylbiphenyl (optically active), C 36° S$_B$ 68° Sc* 78° Ch 85° I
4-[3-fluoro-4-(2-octyloxy)benzoyloxy]-4'-octylbiphenyl (optically active), C 46° Sc* 78° Ch 82.5° I
4-[3-fluoro-4-(2-octyloxy)benzoyloxy]-4'-hexyloxybiphenyl (optically active), C 86° Sc* 107° Ch 118° I
4-[3-fluoro-4-(2-octyloxy)benzoyloxy]-4'-octyloxybiphenyl (optically active), C 64.5° Sc* 97° Ch 99.8° I
4-[3-fluoro-4-(2-octyloxy)benzoyloxy]-4'-dodecyloxybiphenyl (optically active), C 61° Sc* 110° I
4-[3-fluoro-4-(2-methylbutyl)benzoyloxy]-4'-octyloxybiphenyl (optically active), C 113° Sc* 145° Ch 161° I p-octyloxy-phenyl 3-fluoro-4-(7-methoxy)benzoate (optically active), C 52° Sc* 62° I
4-(3-fluoro-4-pentyloxybenzoyloxy)-4'-hexylbiphenyl
4-(3-fluoro-4-hexyloxybenzoyloxy)-4'-hexylbiphenyl
4-(3-fluoro-4-heptyloxybenzoyloxy)-4'-hexylbiphenyl
4-(3-fluoro-4-octyloxybenzoyloxy)-4'-hexylbiphenyl
4-(3-fluoro-4-nonyloxybenzoyloxy)-4'-hexylbiphenyl
4-(3-fluoro-4-(1-methylheptoxy)benzoyloxy)-4'-hexylbiphenyl (optically active)
4-(3-fluoro-4-pentyloxybenzoyloxy)-4'-heptylbiphenyl
4-(3-fluoro-4-hexyloxybenzoyloxy)-4'-heptylbiphenyl
4-(3-fluoro-heptyloxybenzoyloxy)-4'-heptylbiphenyl
4-(3-fluoro-4-octyloxybenzoyloxy)-4'-heptylbiphenyl
4-(3-fluoro-4-nonyloxybenzoyloxy)-4'-heptylbiphenyl
4-(3-fluoro-4-(1-methylheptoxy)benzoyloxy)-4'-heptylbiphenyl (optically active)
4-(3-fluoro-4-pentyloxybenzoyloxy)-4'-octylbiphenyl
4-(3-fluoro-4-hexyloxybenzoyloxy)-4'-octylbiphenyl 4-(3-fluoro-4-heptyloxybenzoyloxy)-4'-octylbiphenyl
4-(3-fluoro-4-octyloxybenzoyloxy)-4'-octylbiphenyl
4-(3-fluoro-4-nonyloxybenzoyloxy)-4'-octylbiphenyl
4-(3-fluoro-4-(1-methylheptoxy)benzoyloxy)-4'-octylbiphenyl (optically active)
4-(3-fluoro-4-pentyloxybenzoyloxy)-4'-nonylbiphenyl
4-(3-fluoro-4-hexyloxybenzoyloxy)-4'-nonylbiphenyl
4-(3-fluoro-4-heptyloxybenzoyloxy)-4'-nonylbiphenyl
4-(3-fluoro-4-octyloxybenzoyloxy)-4'-nonylbiphenyl
4-(3-fluoro-4-nonyloxybenzoyloxy)-4'-nonylbiphenyl
4-(3-fluoro-4-(1-methylheptoxy)benzoyloxy)-4'-nonylbiphenyl (optically active)
4-(3-fluoro-4-pentyloxybenzoyloxy)-4'-pentyloxybiphenyl
4-(3-fluoro-4-hexyloxybenzoyloxy)-4'-pentyloxybiphenyl
4-(3-fluoro-4-heptyloxybenzoyloxy)-4'-pentyloxybiphenyl
4-(3-fluoro-4-octyloxybenzoyloxy)-4'-pentyloxybiphenyl
4-(3-fluoro-4-nonyloxybenzoyloxy)-4'-pentyloxybiphenyl
4-(3-fluoro-4-pentyloxybenzoyloxy)-4'-hexyloxybiphenyl
4-(3-fluoro-4-hexyloxybenzoyloxy)-4'-hexyloxybiphenyl
4-(3-fluoro-4-heptyloxybenzoyloxy)-4'-hexyloxybiphenyl
4-(3-fluoro-4-octyloxybenzoyloxy)-4'-hexyloxybiphenyl
4-(3-fluoro-4-nonyloxybenzoyloxy)-4'-hexyloxybiphenyl
4-(3-chloro-4-pentyloxybenzoyloxy)-4'-heptyloxybiphenyl
4-(3-chloro-4-hexyloxybenzoyloxy)-4'-heptyloxybiphenyl
4-(3-chloro-4-heptyloxybenzoyloxy)-4'-heptyloxybiphenyl
4-(3-chloro-4-octyloxybenzoyloxy)-4'-heptyloxybiphenyl
4-(3-chloro-4-nonyloxybenzoyloxy)-4'-heptyloxybiphenyl
4-(3-fluoro-4-pentyloxybenzoyloxy)-4'-octyloxybiphenyl
4-(3-fluoro-4-hexyloxybenzoyloxy)-4'-octyloxybiphenyl
4-(3-fluoro-4-heptyloxybenzoyloxy)-4'-octyloxybiphenyl, C 110° Sc 167° N 184° I
4-(3-fluoro-4-octyloxybenzoyloxy)-4'-octyloxybiphenyl
4-(3-fluoro-4-nonyloxybenzoyloxy)-4'-octyloxybiphenyl
4-(3-bromo-4-pentyloxybenzoyloxy)-4'-octyloxybiphenyl
4-(3-bromo-4-hexyloxybenzoyloxy)-4'-octyloxybiphenyl
4-(3-bromo-4-heptyloxybenzoyloxy)-4'-octyloxybiphenyl
4-(3-bromo-4-octyloxybenzoyloxy)-4'-octyloxybiphenyl, K 115° Sc 158° N 164° I
4-(3-bromo-4-nonyloxybenzoyloxy)-4'-octyloxybiphenyl
4-(3-bromo-4-(1-methylheptoxy)benzoyloxy)-4'-octyloxybiphenyl (optically active)
4-(3-chloro-4-pentyloxybenzoyloxy)-4'-octyloxybiphenyl
4-(3-chloro-4-hexyloxybenzoyloxy)-4'-octyloxybiphenyl
4-(3-chloro-4-heptyloxybenzoyloxy)-4'-octyloxybiphenyl
4-(3-chloro-4-octyloxybenzoyloxy)-4'-octyloxybiphenyl
4-(3-chloro-4-nonyloxybenzoyloxy)-4'-octyloxybiphenyl
4-(3-chloro-4-(1-methylheptoxy)benzyloxy)-4'-octyloxybiphenyl, C 62° Sc* 97° Ch 98° I, Ps=−166 nC/cm$^2$ (optically active)
4-[3-chloro-4-octyloxybenzoyloxy]-4'-(2-chloro-3-methylbutyryloxy)-biphenyl (optically active), C 79° Sc* 121.5° Ch 146° I
4-(3-fluoro-4-pentylbenzoyloxy)-4'-pentyloxybiphenyl
4-(3-fluoro-4-hexylbenzoyloxy)-4'-pentyloxybiphenyl
4-(3-fluoro-4-heptylbenzoyloxy)-4'-pentyloxybiphenyl
4-(3-fluoro-4-octylbenzoyloxy)-4'-pentyloxybiphenyl
4-(3-fluoro-4-nonylbenzoyloxy)-4'-pentyloxybiphenyl
4-(3-bromo-4-pentylbenzoyloxy)-4'-hexyloxybiphenyl
4-(3-bromo-4-hexylbenzoyloxy)-4'-hexyloxybiphenyl
4-(3-bromo-4-heptylbenzoyloxy)-4'-hexyloxybiphenyl
4-(3-bromo-4-octylbenzoyloxy)-4'-hexyloxybiphenyl
4-(3-bromo-4-nonylbenzoyloxy)-4'-hexyloxybiphenyl
4-(3-chloro-4-pentylbenzoyloxy)-4'-heptyloxybiphenyl
4-(3-chloro-4-hexylbenzoyloxy)-4'-heptyloxybiphenyl
4-(3-chloro-4-heptylbenzoyloxy)-4'-heptyloxybiphenyl
4-(3-chloro-4-octylbenzoyloxy)-4'-heptyloxybiphenyl
4-(3-chloro-4-nonylbenzoyloxy)-4'-heptyloxybiphenyl
4-(3-bromo-4-pentylbenzoyloxy)-4'-octyloxybiphenyl
4-(3-bromo-4-hexylbenzoyloxy)-4'-octyloxybiphenyl
4-(3-bromo-4-heptylbenzoyloxy)-4'-octyloxybiphenyl
4-(3-bromo-4-octylbenzoyloxy)-4'-octyloxybiphenyl, C 72° Sc 123° N 136° I
4-(3-Bromo-4-nonylbenzoyloxy)-4'-octyloxybiphenyl
4-(3-cyano-4-pentylbenzoyloxy)-4'-octyloxybiphenyl
4-(3-cyano-4-hexylbenzoyloxy)-4'-octyloxybiphenyl
4-(3-cyano-4-heptylbenzoyloxy)-4'-octyloxybiphenyl
4-(3-cyano-4-octylbenzoyloxy)-4'-octyloxybiphenyl, C 52° Sc 116° S$_A$ 142° I
4-(3-cyano-4-nonylbenzoyloxy)-4'-octyloxybiphenyl.
4-[3-fluoro-4-octyloxybenzoyloxy]-4'-(4-methylhexyl)-biphenyl (optically active), C 90° Sc* 123° Ch 139° I
4-[3-fluoro-4-dodexyloxybenzoyloxy]-4'-(2-methylbutyloxycarbonyl)-biphenyl (optically active) C 57° Sc* 115° S$_A$ 150° I
4-[3-fluoro-4-decyloxybenzoyloxy]-4'-(2-methylbutyloxycarbonyl)-biphenyl (optically active), C 84° Sc* 118° S$_A$ 152° I
4-[3-fluoro-4-decyloxybenzoyloxy]-4'-(1-methylpentyloxycarbonyl)-biphenyl (optically active), C 88° S$_A$ 136° I
4-[3-fluoro-4-octyloxybenzoyloxy]-4'-(2-methylbutyloxycarbonyl)-biphenyl (optically active), C 98° Sc* 120° S$_A$ 154° N 157° I
4-[3-chloro-4-(octylcarbonyloxy)benzoyloxy]-4'-(2-chloro-3-methylpentyloxycarbonyl)-biphenyl (optically active), C 87° Sc* 98° N 126° I
4-[3-chloro-4-(octylcarbonyloxy)benzoyloxy]-4'-(2-chloro-3-methylbutyryloxy)-biphenyl (optically active), C 85° Sc* 123° N 138° I

EXAMPLE 2

4-(3-Bromo-4-n-octyloxybenzoyloxy)-4'-n-pentylcyclohexyl with C 41° S$_A$ 116° N 145° I is obtained analogously to Example 1 by reaction of 4'-n-pentyl-4-hydroxybicyclohexyl with 3-bromo-4-n-octyloxybenzoyl chloride.

The following compounds are prepared analogously:

4-(3-bromo-4-propyloxybenzoyloxy)-4'-pentylbicyclohexyl
4-(3-bromo-4-butyloxybenzoyloxy)-4'-pentylbicyclohexyl
4-(3-bromo-4-pentyloxybenzoyloxy)-4'-pentylbicyclohexyl
4-(3-bromo-4-hexyloxybenzoyloxy)-4'-pentylbicyclohexyl
4-(3-bromo-4-heptyloxybenzoyloxy)-4'-pentylbicyclohexyl
4-(3-bromo-4-nonyloxybenzoyloxy)-4'-pentylbicyclohexyl
4-(3-bromo-4-propyloxybenzoyloxy)-4'-butylbicyclohexyl
4-(3-bromo-4-butyloxybenzoyloxy)-4'-butylbicyclohexyl
4-(3-bromo-4-pentyloxybenzoyloxy)-4'-butylbicyclohexyl
4-(3-bromo-4-hexyloxybenzoyloxy)-4'-butylbicyclohexyl
4-(3-bromo-4-heptyloxybenzoyloxy)-4'-butylbicyclohexyl
4-(3-bromo-4-octyloxybenzoyloxy)-4'-butylbicyclohexyl
4-(3-bromo-4-nonyloxybenzoyloxy)-4'-butylbicyclohexyl
4-(3-bromo-4-propyloxybenzoyloxy)-4'-hexylbicyclohexyl
4-(3-bromo-4-butyloxybenzoyloxy)-4'-hexylbicyclohexyl
4-(3-bromo-4-pentyloxybenzoyloxy)-4'-hexylbicyclohexyl
4-(3-bromo-4-hexyloxybenzoyloxy)-4'-hexylbicyclohexyl
4-(3-bromo-4-heptyloxybenzoyloxy)-4'-hexylbicyclohexyl
4-(3-bromo-4-octyloxybenzoyloxy)-4'-hexylbicyclohexyl
4-(3-bromo-4-nonyloxybenzoyloxy)-4'-hexylbicyclohexyl
4-(3-fluoro-4-propyloxybenzoyloxy)-4'-heptylbicyclohexyl
4-(3-fluoro-4-butyloxybenzoyloxy)-4'-heptylbicyclohexyl
4-(3-fluoro-4-pentyloxybenzoyloxy)-4'-heptylbicyclohexyl
4-(3-fluoro-4-hexyloxybenzoyloxy)-4'-heptylbicyclohexyl
4-(3-fluoro-4-heptyloxybenzoyloxy)-4'-heptylbicyclohexyl
4-(3-fluoro-4-octyloxybenzoyloxy)-4'-heptylbicyclohexyl
4-(3-fluoro-4-nonyloxybenzoyloxy)-4'-heptylbicyclohexyl
4-(3-fluoro-4-propyloxybenzoyloxy)-4'-octylbicyclohexyl
4-(3-fluoro-4-butyloxybenzoyloxy)-4'-octylbicyclohexyl
4-(3-fluoro-4-pentyloxybenzoyloxy)-4'-octylbicyclohexyl
4-(3-fluoro-4-hexyloxybenzoyloxy)-4'-octylbicyclohexyl
4-(3-fluoro-4-heptyloxybenzoyloxy)-4'-octylbicyclohexyl
4-(3-fluoro-4-octyloxybenzoyloxy)-4'-octylbicyclohexyl
4-(3-fluoro-4-nonyloxybenzoyloxy)-4'-octylbicyclohexyl
4-(3-chloro-4-propylbenzoyloxy)-4'-nonylbicyclohexyl
4-(3-chloro-4-butylbenzoyloxy)-4'-nonylbicyclohexyl
4-(3-chloro-4-pentylbenzoyloxy)-4'-nonylbicyclohexyl
4-(3-chloro-4-hexylbenzoyloxy)-4'-nonylbicyclohexyl
4-(3-chloro-4-heptylbenzoyloxy)-4'-nonylbicyclohexyl
4-(3-chloro-4-octylbenzoyloxy)-4'-nonylbicyclohexyl
4-(3-chloro-4-nonylbenzoyloxy)-4'-nonylbicyclohexyl
4-(3-cyano-4-pentyloxybenzoyloxy)-4'-pentylbicyclohexyl
4-(3-cyano-4-hexyloxybenzoyloxy)-4'-pentylbicyclohexyl
4-(3-cyano-4-heptyloxybenzoyloxy)-4'-pentylbicyclohexyl
4-(3-cyano-4-octyloxybenzoyloxy)-4'-pentylbicyclohexyl C 64° $S_A$ 141° N 146° I
4-(3-cyano-4-nonyloxybenzoyloxy)-4'-pentylbicyclohexyl
4-(3-cyano-4-pentyloxybenzoyloxy)-4'-hexylbicyclohexyl
4-(3-cyano-4-hexyloxybenzoyloxy)-4'-hexylbicyclohexyl
4-(3-cyano-4-heptyloxybenzoyloxy)-4'-hexylbicyclohexyl
4-(3-cyano-4-octyloxybenzoyloxy)-4'-hexylbicyclohexyl
4-(3-cyano-4-nonyloxybenzoyloxy)-4'-hexylbicyclohexyl
4-(3-cyano-4-pentyloxybenzoyloxy)-4'-octylbicyclohexyl
4-(3-cyano-4-hexyloxybenzoyloxy)-4'-octylbicyclohexyl
4-(3-cyano-4-heptyloxybenzoyloxy)-4'-octylbicyclohexyl
4-(3-cyano-4-octyloxybenzoyloxy)-4'-octylbicyclohexyl
4-(3-cyano-4-nonyloxybenzoyloxy)-4'-octylbicyclohexyl.

EXAMPLE 3

Starting from 4'-n-pentyl-4-hydroxybiphenyl and 3-fluoro-4-(4-n-pentylcyclohexyl)benzoyl chloride, 4-[3-fluoro-4-(4-n-pentylcyclohexyl)benzoyloxy]-4'-n-pentylbiphenyl, m.p. 122°, Sc 111° N<275 I is obtained analogously to Example 1.

The following compounds are prepared analogously:
4-[3-fluoro-4-(4-hexylcyclohexyl)benzoyloxy]-4'-pentylbiphenyl
4-[3-fluoro-4-(4-heptylcyclohexyl)benzoyloxy]-4'-pentylbiphenyl
4-[3-fluoro-4-(4-octylcyclohexyl)benzoyloxy]-4'-pentylbiphenyl
4-[3-fluoro-4-(4-nonylcyclohexyl)benzoyloxy]-4'-pentylbiphenyl
4-[3-fluoro-4-(4-pentylcyclohexyl)benzoyloxy]-4'-hexylbiphenyl
4-[3-fluoro-4-(4-hexylcyclohexyl)benzoyloxy]-4'-hexylbiphenyl
4-[3-fluoro-4-(4-heptylcyclohexyl)benzoyloxy]-4'-hexylbiphenyl
4-[3-fluoro-4-(4-octylcyclohexyl)benzoyloxy]-4'-hexylbiphenyl
4-[3-fluoro-4-(4-nonylcyclohexyl)benzoyloxy]-4'-hexylbiphenyl
4-[3-fluoro-4-(4-pentylcyclohexyl)benzoyloxy]-4'-pentoxybiphenyl
4-[3-fluoro-4-(4-hexylcyclohexyl)benzoyloxy]-4'-pentoxybiphenyl 4-[3-fluoro-4-(4-heptylcyclohexyl)benzoyloxy]-4'-pentoxybiphenyl
4-[3-fluoro-4-(4-octylcyclohexyl)benzoyloxy]-4'-pentoxybiphenyl
4-[3-fluoro-4-(4-nonylcyclohexyl)benzoyloxy]-4'-pentoxybiphenyl
4-[3-cyano-4-(4-pentylcyclohexyl)benzoyloxy]-4'-hexoxybiphenyl
4-[3-cyano-4-(4-hexylcyclohexyl)benzoyloxy]-4'-hexoxybiphenyl
4-[3-cyano-4-(4-heptylcyclohexyl)benzoyloxy]-4'-hexoxybiphenyl
4-[3-cyano-4-(4-octylcyclohexyl)benzoyloxy]-4'-hexoxybiphenyl
4-[3-cyano-4-(4-nonylcyclohexyl)benzoyloxy]-4'-hexoxybiphenyl
4-[3-cyano-4-(4-pentylcyclohexyl)benzoyloxy]-4'-heptoxybiphenyl
4-[3-cyano-4-(4-hexylcyclohexyl)benzoyloxy]-4'-heptoxybiphenyl
4-[3-cyano-4-(4-heptylcyclohexyl)benzoyloxy]-4'-heptoxybiphenyl
4-[3-cyano-4-(4-octylcyclohexyl)benzoyloxy]-4'-heptoxybiphenyl
4-[3-cyano-4-(4-nonylcyclohexyl)benzoyloxy]-4'-heptoxybiphenyl
4-[3-chloro-4-(4-pentylcyclohexyl)benzoyloxy]-4'-octoxybiphenyl
4-[3-chloro-4-(4-hexylcyclohexyl)benzoyloxy]-4'-octoxybiphenyl
4-[3-chloro-4-(4-heptylcyclohexyl)benzoyloxy]-4'-octoxybiphenyl
4-[3-chloro-4-(4-octylcyclohexyl)benzoyloxy]-4'-octoxybiphenyl
4-[3-chloro-4-(4-nonylcyclohexyl)benzoyloxy]-4'-octoxybiphenyl
4-[3-chloro-4-(4-pentylcyclohexyl)benzoyloxy]-4'-octylbiphenyl
4-[3-chloro-4-(4-hexylcyclohexyl)benzoyloxy]-4'-octylbiphenyl
4-[3-chloro-4-(4-heptylcyclohexyl)benzoyloxy]-4'-octylbiphenyl
4-[3-chloro-4-(4-octylcyclohexyl)benzoyloxy]-4'-octylbiphenyl
4-[3-chloro-4-(4-nonylcyclohexyl)benzoyloxy]-4'-octylbiphenyl
4-[3-chloro-4-(4-pentylcyclohexyl)benzoyloxy]-4'-nonyloxybiphenyl
4-[3-chloro-4-(4-hexylcyclohexyl)benzoyloxy]-4'-nonyloxybiphenyl
4-[3-chloro-4-(4-heptylcyclohexyl)benzoyloxy]-4'-nonyloxybiphenyl
4-[3-chloro-4-(4-octylcyclohexyl)benzoyloxy]-4'-nonyloxybiphenyl
4-[3-chloro-4-(4-nonylcyclohexyl)benzoyloxy]-4'-nonyloxybiphenyl
4-[3-fluoro-4-(4-hexylphenyl)benzoyloxy]-4'-pentylbiphenyl
4-[3-fluoro-4-(4-pentylphenyl)benzoyloxy]-4'-pentylbiphenyl
4-[3-fluoro-4-(4-heptylphenyl)benzoyloxy]-4'-pentylbiphenyl
4-[3-fluoro-4-(4-octylphenyl)benzoyloxy]-4'-pentylbiphenyl
4-[3-fluoro-4-(4-nonylphenyl)benzoyloxy]-4'-pentylbiphenyl
4-[3-fluoro-4-(4-hexylphenyl)benzoyloxy]-4'-hexylbiphenyl
4-[3-fluoro-4-(4-pentylphenyl)benzoyloxy]-4'-hexylbiphenyl
4-[3-fluoro-4-(4-heptylphenyl)benzoyloxy]-4'-hexylbiphenyl
4-[3-fluoro-4-(4-octylphenyl)benzoyloxy]-4'-hexylbiphenyl
4-[3-fluoro-4-(4-nonylphenyl)benzoyloxy]-4'-hexylbiphenyl
4-[3-fluoro-4-(4-hexylphenyl)benzoyloxy]-4'-pentoxybiphenyl
4-[3-fluoro-4-(4-pentylphenyl)benzoyloxy]-4'-pentoxybiphenyl
4-[3-fluoro-4-(4-heptylphenyl)benzoyloxy]-4'-pentoxybiphenyl
4-[3-fluoro-4-(4-octylphenyl)benzoyloxy]-4'-pentoxybiphenyl
4-[3-fluoro-4-(4-nonylphenyl)benzoyloxy]-4'-pentoxybiphenyl
4-[3-cyano-4-(4-hexylphenyl)benzoyloxy]-4'-hexoxybiphenyl
4-[3-cyano-4-(4-pentylphenyl)benzoyloxy]-4'-hexoxybiphenyl
4-[3-cyano-4-(4-heptylphenyl)benzoyloxy]-4'-hexoxybiphenyl
4-[3-cyano-4-(4-octylphenyl)benzoyloxy]-4'-hexoxybiphenyl
4-[3-cyano-4-(4-nonylphenyl)benzoyloxy]-4'-hexoxybiphenyl
4-[3-cyano-4-(4-hexylphenyl)benzoyloxy]-4'-octoxybiphenyl
4-[3-cyano-4-(4-pentylphenyl)benzoyloxy]-4'-octoxybiphenyl
4-[3-cyano-4-(4-heptylphenyl)benzoyloxy]-4'-octoxybiphenyl
4-[3-cyano-4-(4-octylphenyl)benzoyloxy]-4'-octoxybiphenyl
4-[3-cyano-4-(4-nonylphenyl)benzoyloxy]-4'-octoxybiphenyl
4-[3-chloro-4-(4-hexylphenyl)benzoyloxy]-4'-heptoxybiphenyl
4-[3-chloro-4-(4-pentylphenyl)benzoyloxy]-4'-heptoxybiphenyl
4-[3-chloro-4-(4-heptylphenyl)benzoyloxy]-4'-heptoxybiphenyl
4-[3-chloro-4-(4-octylphenyl)benzoyloxy]-4'-heptoxybiphenyl
4-[3-chloro-4-(4-nonylphenyl)benzoyloxy]-4'-heptoxybiphenyl
4-[3-chloro-4-(4-hexylphenyl)benzoyloxy]-4'-octylbiphenyl
4-[3-chloro-4-(4-pentylphenyl)benzoyloxy]-4'-octylbiphenyl
4-[3-chloro-4-(4-heptylphenyl)benzoyloxy]-4'-octylbiphenyl
4-[3-chloro-4-(4-octylphenyl)benzoyloxy]-4'-octylbiphenyl
4-[3-chloro-4-(4-nonylphenyl)benzoyloxy]-4'-octylbiphenyl
4-[3-chloro-4-(4-hexylphenyl)benzoyloxy]-4-nonyloxybiphenyl
4-[3-chloro-4-(4-pentylphenyl)benzoyloxy]-4'-nonyloxybiphenyl
4-[3-chloro-4-(4-heptylphenyl)benzoyloxy]-4'-nonyloxybiphenyl
4-[3-chloro-4-(4-octylphenyl)benzoyloxy]-4'-nonyloxybiphenyl
4-[3-chloro-4-(4-nonylphenyl)benzoyloxy]-4'-nonyloxybiphenyl p-pentylphenyl 4-[3-chloro-4-hexylphenyl]-benzoate
p-pentylphenyl 4-[3-chloro-4-pentylphenyl]-benzoate
p-pentylphenyl 4-[3-chloro-4-heptylphenyl]-benzoate
p-pentylphenyl 4-[3-chloro-4-octylphenyl]-benzoate
p-pentylphenyl 4-[3-chloro-4-nonylphenyl]-benzoate
p-pentylphenyl 4-[3-chloro-4-hexyloxyphenyl]-benzoate
p-pentylphenyl 4-[3-chloro-4-pentyloxyphenyl]-benzoate
p-pentylphenyl 4-[3-chloro-4-heptyloxyphenyl]-benzoate
p-pentylphenyl 4-[3-chloro-4-octyloxyphenyl]-benzoate
p-pentylphenyl 4-[3-chloro-4-nonyloxyphenyl]-benzoate
p-pentylphenyl 4-[3-fluoro-4-hexylphenyl]-benzoate
p-pentylphenyl 4-[3-fluoro-4-pentylphenyl]-benzoate
p-pentylphenyl 4-[3-fluoro-4-heptylphenyl]-benzoate
p-pentylphenyl 4-[3-fluoro-4-octylphenyl]-benzoate
p-pentylphenyl 4-[3-fluoro-4-nonylphenyl]-benzoate
p-pentylphenyl 4-[3-cyano-4-hexyloxyphenyl]-benzoate
p-pentylphenyl 4-[3-cyano-4-pentyloxyphenyl]-benzoate
p-pentylphenyl 4-[3-cyano-4-heptyloxyphenyl]-benzoate
p-pentylphenyl 4-[3-cyano-4-octyloxyphenyl]-benzoate
p-pentylphenyl 4-[3-cyano-4-nonyloxyphenyl]-benzoate
p-pentyloxyphenyl 4-[3-chloro-4-hexylphenyl]-benzoate
p-pentyloxyphenyl 4-[3-chloro-4-pentylphenyl]-benzoate
p-pentyloxyphenyl 4-[3-chloro-4-heptylphenyl]-benzoate
p-pentyloxyphenyl 4-[3-chloro-4-octylphenyl]-benzoate
p-pentyloxyphenyl 4-[3-chloro-4-nonylphenyl]-benzoate
p-hexyloxyphenyl 4-[3-fluoro-4-hexylphenyl]-benzoate
p-hexyloxyphenyl 4-[3-fluoro-4-pentylphenyl]-benzoate
p-hexyloxyphenyl 4-[3-fluoro-4-heptylphenyl]-benzoate
p-hexyloxyphenyl 4-[3-fluoro-4-octylphenyl]-benzoate
p-hexyloxyphenyl 4-[3-fluoro-4-nonylphenyl]-benzoate
p-heptyloxyphenyl 4-[3-fluoro-4-hexyloxyphenyl]-benzoate
p-heptyloxyphenyl 4-[3-fluoro-4-pentyloxyphenyl]-benzoate
p-heptyloxyphenyl 4-[3-fluoro-4-heptyloxyphenyl]-benzoate
p-heptyloxyphenyl 4-[3-fluoro-4-octyloxyphenyl]-benzoate
p-heptyloxyphenyl 4-[3-fluoro-4-nonyloxyphenyl]-benzoate
p-octyloxyphenyl 4-[3-cyano-4-hexylphenyl]-benzoate
p-octyloxyphenyl 4-[3-cyano-4-pentylphenyl]-benzoate
p-octyloxyphenyl 4-[3-cyano-4-heptylphenyl]-benzoate
p-octyloxyphenyl 4-[3-cyano-4-octylphenyl]-benzoate
p-octyloxyphenyl 4-[3-cyano-4-nonylphenyl]-benzoate
p-nonyloxyphenyl 4-[3-fluoro-4-hexylphenyl]-benzoate
p-nonyloxyphenyl 4-[3-fluoro-4-pentylphenyl]-benzoate
p-nonyloxyphenyl 4-[3-fluoro-4-heptylphenyl]-benzoate
p-nonyloxyphenyl 4-[3-fluoro-4-octylphenyl]-benzoate
p-nonyloxyphenyl 4-[3-fluoro-4-nonylphenyl]-benzoate
p-decylphenyl 4-[3-chloro-4-hexyloxyphenyl]-benzoate
p-decylphenyl 4-[3-chloro-4-pentyloxyphenyl]-benzoate
p-decylphenyl 4-[3-chloro-4-heptyloxyphenyl]-benzoate
p-decylphenyl 4-[3-chloro-4-octyloxyphenyl]-benzoate
p-decylphenyl 4-[3-chloro-4-nonyloxyphenyl]-benzoate
p-(2-methylbutyloxycarbonyl)phenyl 4-[3-fluoro-4-octyloxyphenyl]-benzoate (optically active), C 62° Sc* 125° $S_A$ 171° I
p-(2-methylbutyloxycarbonyl)phenyl 4-[3-fluoro-4-decyloxyphenyl]-benzoate (optically active), C 54° Sc* 124° $S_A$ 166° I
p-(2-methylbutyloxycarbonyl)phenyl 4-[3-chloro-4-octyloxyphenyl]-benzoate (optically active), C 40° Sc* 59° $S_A$ 146° I
p-pentylphenyl 4-[3-fluoro-4-(6-methyloctyloxy)-phenyl]benzoate (optically active), C 56° Sc* 140° $S_A$ 158° I
p-octylphenyl 4-[3-fluoro-4-(6-methyloctyloxy)phenyl]-benzoate (optically active), C 61° Sc* 144° $S_A$ 151° I
p-heptyloxyphenyl 4-[3-fluoro-4-(6-methyloctyloxy)-phenyl]benzoate (optically active), C 83° Sc* 168° $S_A$ 172° I
p-dodecyloxyphenyl 4-[3-fluoro-4-(6-methyloctyloxy)-phenyl]-benzoate (optically active), C 66° Sc* 158° $S_A$ 161° I
p-pentyloxycarbonylphenyl 4-[3-fluoro-4-(6-methyloctyloxy)phenyl]-benzoate (optically active), C 70° Sc* 134° $S_A$ 170° I
p-pentyloxyphenyl 4-[3-fluoro-4-(2-octyloxy)phenyl]-benzoate (optically active), C 56° Sc* 98° Ch 112° I
p-octyloxyphenyl 4-[3-fluoro-4-(2-octyloxy)phenyl]-benzoate (optically active), C 52° Sc* 104° Ch 109° I
p-(2-methylbutyloxy)-phenyl 4-[3-chloro-4-octyloxyphenyl]-benzoate (optically active), C 78° Sc* 114° $S_A$ 138° I
p-(6-methyloctyloxy)-phenyl 4-[3-fluoro-4-octyloxyphenyl]-benzoate (optically active), C 80° Sc* 164° $S_A$ 174° I.

EXAMPLE 4

6.0 mmol of DCC (dicyclohexylcarbodiimide) are added to 5.5 mmol of 4-[3-chloro-4-octyloxybenzoyloxy]-4'-hydroxybiphenyl (which can be prepared by esterification of 4,4'-dihydroxybiphenyl with 3-chloro-4-octyloxybenzoic acid in the presence of DCC), 6.0 mmol of 2-chloro-3-methylbutyric acid and 100 ml of methylene chloride at room temperature, with stirring.

After stirring for 24 h, the crude mixture is filtered with methylene chloride over a silica gel column. After evaporation and recrystallization, optically active 4-[3-chloro-4-octyloxybenzoyloxy]-4'-(2-chloro-3-methylbutyryloxy)-biphenyl with C 79°, Sc* 121.5°, Ch 146° I is obtained.

The following optically active compounds are prepared analogously:
4-[3-chloro-4-heptyloxybenzoyloxy]-4'-(2-chloro-3-methylbutyryloxy)-biphenyl
4-[3-chloro-4-hexyloxybenzoyloxy]-4'-(2-chloro-3-methylbutyryloxy)-biphenyl
4-[3-chloro-4-pentyloxybenzoyloxy]-4'-(2-chloro-3-methylbutyryloxy)-biphenyl
4-[3-chloro-4-nonyloxybenzoyloxy]-4'-(2-chloro-3-methylbutyryloxy)-biphenyl
4-[3-chloro-4-decyloxybenzoyloxy]-4'-(2-chloro-3-methylbutyryloxy)-biphenyl
4-[3-chloro-4-pentylbenzoyloxy]-4'-(2-chloro-3-methylbutyryloxy)-biphenyl
4-[3-chloro-4-hexylbenzoyloxy]-4'-(2-chloro-3-methylbutyryloxy)-biphenyl 4-[3-chloro-4-heptylbenzoyloxy]-4'-(2-chloro-3-methylbutyryloxy)-biphenyl
4-[3-chloro-4-octylbenzoyloxy]-4'-(2-chloro-3-methylbutyryloxy)-biphenyl
4-[3-chloro-4-nonylbenzoyloxy]-4'-(2-chloro-3-methylbutyryloxy)-biphenyl
4-[3-chloro-4-decylbenzoyloxy]-4'-(2-chloro-3-methylbutyryloxy)-biphenyl
4-[3-fluoro-4-pentyloxybenzoyloxy]-4'-(2-chloro-3-methylbutyryloxy)-biphenyl
4-[3-fluoro-4-hexyloxybenzoyloxy]-4'-(2-chloro-3-methylbutyryloxy)-biphenyl
4-[3-fluoro-4-heptyloxybenzoyloxy]-4'-(2-chloro-3-methylbutyryloxy)-biphenyl
4-[3-fluoro-4-octyloxybenzoyloxy]-4'-(2-chloro-3-methylbutyryloxy)-biphenyl
4-[3-fluoro-4-nonyloxybenzoyloxy]-4'-(2-chloro-3-methylbutyryloxy)-biphenyl
4-[3-fluoro-4-decyloxybenzoyloxy]-4'-(2-chloro-3-methylbutyryloxy)-biphenyl
4-[3-fluoro-4-pentylbenzoyloxy]-4'-(2-chloro-3-methylbutyryloxy)-biphenyl
4-[3-fluoro-4-hexylbenzoyloxy]-4'-(2-chloro-3-methylbutyryloxy)-biphenyl
4-[3-fluoro-4-heptylbenzoyloxy]-4'-(2-chloro-3-methylbutyryloxy)-biphenyl
4-[3-fluoro-4-octylbenzoyloxy]-4'-(2-chloro-3-methylbutyryloxy)-biphenyl
4-[3-fluoro-4-nonylbenzoyloxy]-4'-(2-chloro-3-methylbutyryloxy)-biphenyl
4-[3-fluoro-4-decylbenzoyloxy]-4'-(2-chloro-3-methylbutyryloxy)-biphenyl
4-[3-cyano-4-pentyloxybenzoyloxy]-4'-(2-chloro-3-methylbutyryloxy)-biphenyl
4-[3-cyano-4-hexyloxybenzoyloxy]-4'-(2-chloro-3-methylbutyryloxy)-biphenyl
4-[3-cyano-4-heptyloxybenzoyloxy]-4'-(2-chloro-3-methylbutyryloxy)-biphenyl
4-[3-cyano-4-octyloxybenzoyloxy]-4'-(2-chloro-3-methylbutyryloxy)-biphenyl
4-[3-cyano-4-nonyloxybenzoyloxy]-4'-(2-chloro-3-methylbutyryloxy)-biphenyl
4-[3-cyano-4-decyloxybenzoyloxy]-4'-(2-chloro-3-methylbutyryloxy)-biphenyl
4-[3-cyano-4-pentylbenzoyloxy]-4'-(2-chloro-3-methylbutyryloxy)-biphenyl
4-[3-cyano-4-hexylbenzoyloxy]-4'-(2-chloro-3-methylbutyryloxy)-biphenyl
4-[3-cyano-4-heptylbenzoyloxy]-4'-(2-chloro-3-methylbutyryloxy)-biphenyl
4-[3-cyano-4-octylbenzoyloxy]-4'-(2-chloro-3-methylbutyryloxy)-biphenyl
4-[3-cyano-4-nonylbenzoyloxy]-4'-(2-chloro-3-methylbutyryloxy)-biphenyl
4-[3-cyano-4-decylbenzoyloxy]-4'-(2-chloro-3-methylbutyryloxy)-biphenyl

EXAMPLE 5

0.012 m of DCC is added to 0.01 m of 4-pentylphenyl 3-chloro-4-hydroxybenzoate (obtainable by esterification of 3-chloro-4-hydroxybenzoic acid with 4-pentylphenyl with the addition of sulfuric acid and boric acid, J. org. Chem. Vol. 40 (1975) 2998), 0.012 m of 2-chloro-3-methylbutyric acid and 100 ml of methylene chloride at room temperature, with stirring. Further working up is carried out analogously to Example 3 to give 4-pentylphenyl 3-chloro-4-(2-chloro-3-methylbutyryloxy)-benzoate (optically active).

The following optically active compounds are prepared analogously:
4-hexylphenyl 3-chloro-4-(2-chloro-3-methylbutyryloxy)-benzoate
4-heptylphenyl 3-chloro-4-(2-chloro-3-methylbutyryloxy)-benzoate
4-octylphenyl 3-chloro-4-(2-chloro-3-methylbutyryloxy)-benzoate
4-nonylphenyl 3-chloro-4-(2-chloro-3-methylbutyryloxy)-benzoate
4-decylphenyl 3-chloro-4-(2-chloro-3-methylbutyryloxy)-benzoate
4-pentyloxyphenyl 3-chloro-4-(2-chloro-3-methylbutyryloxy)-benzoate
4-hexyloxyphenyl 3-chloro-4-(2-chloro-3-methylbutyryloxy)-benzoate
4-heptyloxyphenyl 3-chloro-4-(2-chloro-3-methylbutyryloxy)-benzoate
4-octyloxyphenyl 3-chloro-4-(2-chloro-3-methylbutyryloxy)-benzoate
4-nonyloxyphenyl 3-chloro-4-(2-chloro-3-methylbutyryloxy)-benzoate
4-decyloxyphenyl 3-chloro-4-(2-chloro-3-methylbutyryloxy)-benzoate
4-pentylphenyl 3-fluoro-4-(2-chloro-3-methylbutyryloxy)-benzoate
4-hexylphenyl 3-fluoro-4-(2-chloro-3-methylbutyryloxy)-benzoate
4-heptylphenyl 3-fluoro-4-(2-chloro-3-methylbutyryloxy)-benzoate
4-octylphenyl 3-fluoro-4-(2-chloro-3-methylbutyryloxy)-benzoate
4-nonylphenyl 3-fluoro-4-(2-chloro-3-methylbutyryloxy)-benzoate
4-decylphenyl 3-fluoro-4-(2-chloro-3-methylbutyryloxy)-benzoate
4-pentyloxyphenyl 3-fluoro-4-(2-chloro-3-methylbutyryloxy)-benzoate
4-hexyloxyphenyl 3-fluoro-4-(2-chloro-3-methylbutyryloxy)-benzoate
4-heptyloxyphenyl 3-fluoro-4-(2-chloro-3-methylbutyryloxy)-benzoate
4-octyloxyphenyl 3-fluoro-4-(2-chloro-3-methylbutyryloxy)-benzoate
4-nonyloxyphenyl 3-fluoro-4-(2-chloro-3-methylbutyryloxy)-benzoate
4-decyloxyphenyl 3-fluoro-4-(2-chloro-3-methylbutyryloxy)-benzoate
4-pentylphenyl 3-cyano-4-(2-chloro-3-methylbutyryloxy)-benzoate
4-hexylphenyl 3-cyano-4-(2-chloro-3-methylbutyryloxy)-benzoate
4-heptylphenyl 3-cyano-4-(2-chloro-3-methylbutyryloxy)-benzoate
4-octylphenyl 3-cyano-4-(2-chloro-3-methylbutyryloxy)-benzoate
4-nonylphenyl 3-cyano-4-(2-chloro-3-methylbutyryloxy)-benzoate
4-decylphenyl 3-cyano-4-(2-chloro-3-methylbutyryloxy)-benzoate
4-pentyloxyphenyl 3-cyano-4-(2-chloro-3-methylbutyryloxy)-benzoate
4-hexyloxyphenyl 3-cyano-4-(2-chloro-3-methylbutyryloxy)-benzoate
4-heptyloxyphenyl 3-cyano-4-(2-chloro-3-methylbutyryloxy)-benzoate
4-octyloxyphenyl 3-cyano-4-(2-chloro-3-methyl- 4-nonyloxyphenyl 3-cyano-4-(2-chloro-3-methylbutyryloxy)-benzoate
4-decyloxyphenyl 3-cyano-4-(2-chloro-3-methylbutyryloxy)-benzoate
(4'-pentylbiphenyl-4-yl) 3-chloro-4-(2-chloro-3-methylbutyryloxy)-benzoate
(4'-hexylbiphenyl-4-yl) 3-chloro-4-(2-chloro-3-methylbutyryloxy)-benzoate
(4'-heptylbiphenyl-4-yl) 3-chloro-4-(2-chloro-3-methylbutyryloxy)-benzoate
(4'-octylbiphenyl-4-yl) 3-chloro-4-(2-chloro-3-methylbutyryloxy)-benzoate
(4'-nonylbiphenyl-4-yl) 3-chloro-4-(2-chloro-3-methylbutyryloxy)-benzoate
(4'-decylbiphenyl-4-yl) 3-chloro-4-(2-chloro-3-methylbutyryloxy)-benzoate
(4'-pentyloxybiphenyl-4-yl) 3-chloro-4-(2-chloro-3-methylbutyryloxy)-benzoate
(4'-hexyloxybiphenyl-4-yl) 3-chloro-4-(2-chloro-3-methylbutyryloxy)-benzoate
(4'-heptyloxybiphenyl-4-yl) 3-chloro-4-(2-chloro-3-methylbutyryloxy)-benzoate
(4'-octyloxybiphenyl-4-yl) 3-chloro-4-(2-chloro-3-methylbutyryloxy)-benzoate
(4'-nonyloxybiphenyl-4-yl) 3-chloro-4-(2-chloro-3-methylbutyryloxy)-benzoate
(4'-decyloxybiphenyl-4-yl) 3-chloro-4-(2-chloro-3-methylbutyryloxy)-benzoate
(4'-pentylbiphenyl-4-yl) 3-fluoro-4-(2-chloro-3-methylbutyryloxy)-benzoate
(4'-hexylbiphenyl-4-yl) 3-fluoro-4-(2-chloro-3-methylbutyryloxy)-benzoate
(4'-heptylbiphenyl-4-yl) 3-fluoro-4-(2-chloro-3-methylbutyryloxy)-benzoate
(4'-octylbiphenyl-4-yl) 3-fluoro-4-(2-chloro-3-methylbutyryloxy)-benzoate
(4'-nonylbiphenyl-4-yl) 3-fluoro-4-(2-chloro-3-methylbutyryloxy)-benzoate
(4'-decylbiphenyl-4-yl) 3-fluoro-4-(2-chloro-3-methylbutyryloxy)-benzoate
(4'-pentyloxybiphenyl-4-yl) 3-fluoro-4-(2-chloro-3-methylbutyryloxy)-benzoate
(4'-hexyloxybiphenyl-4-yl) 3-fluoro-4-(2-chloro-3-methylbutyryloxy)-benzoate
(4'-heptyloxybiphenyl-4-yl) 3-fluoro-4-(2-chloro-3-methylbutyryloxy)-benzoate
(4'-octyloxybiphenyl-4-yl) 3-fluoro-4-(2-chloro-3-methylbutyryloxy)-benzoate
(4'-nonyloxybiphenyl-4-yl) 3-fluoro-4-(2-chloro-3-methylbutyryloxy)-benzoate
(4'-decyloxybiphenyl-4-yl) 3-fluoro-4-(2-chloro-3-methylbutyryloxy)-benzoate

EXAMPLE A

A liquid crystal phase consisting of
35% of 4-(3-bromo-4-octylbenzoyloxy)-4'-octyloxybiphenyl,
30% of 4-(3-cyano-4-octylbenzoyloxy)-4'-octyloxybiphenyl,
25% of 4-[3-chloro-4-(1-methylheptoxy)benzoyloxy]-4'-octyloxybiphenyl (optically active) and
10% of 4-(3-bromo-4-octyloxybenzoyloxy)-4'-pentylbicyclohexyl
has C 35° S$_C$* 103° S$_A$* 111° Ch 129° I and a spontaneous polarization Ps of −22 nC/cm².

EXAMPLE B

A liquid crystal phase consisting of
45% of 4-(3-bromo-4-octylbenzoyloxy)-4'-octyloxybiphenyl,
25% of 4-(3-fluoro-4-heptyloxybenzoyloxy)-4'-octyloxybiphenyl and
30% of 4-[3-chloro-4-(1-methylheptyloxy)benzoyloxy]-4'-octyloxybiphenyl (optically active)
has C 37° Sc* 106° Ch 123° I and a spontaneous polarization Ps of −27 nC/cm².

EXAMPLE C

A liquid crystal mixture consisting of
15% of 4-(3-fluoro-4-heptyloxybenzoyloxy)-4'-pentylbiphenyl,
15% of 4-(3-bromo-4-octyloxybenzoyloxy)-4'-octyloxybiphenyl
25% of 4-[3-chloro-4-(1-methylheptyloxy)benzoyloxy]-4'-octylbiphenyl (optically active),
35% of 4-(3-cyano-4-octylbenzoyloxy)-4'-octyloxybiphenyl and
10% of 4-(3-cyano-4-octyloxybenzoyloxy)-4'-pentylbicyclohexyl
has C 23° Sc* 89° S$_A$* 98° Ch 117° I and a spontaneous polarization Ps of −23 nC/cm².

EXAMPLE D

A liquid crystal phase consisting of
2% of 4-[3-chloro-4-(1-methylheptyloxy)benzoyloxy]-4'-octyloxybiphenyl (optically active) and
98% of a mixture of
16% of p-trans-4-propylcyclohexylbenzonitrile,
10% of p-trans-4-butylcyclohexylbenzonitrile,
11% of trans-1-p-ethoxyphenyl-4-propylcyclohexane,
9% of trans,trans-4-propyl-4'-propoxycyclohexylcyclohexane,
8% of trans,trans-4-pentyl-4'-methoxycyclohexylcyclohexane,
8% of trans,trans-4-pentyl-4'-ethoxycyclohexylcyclohexane,
4% of trans-4-propylcyclohexyl trans,trans-4-propylcyclohexyl-cyclohexane-4'-carboxylate,
4% of trans-4-pentylcyclohexyl trans,trans-4-propylcyclohexyl-cyclohexane-4'-carboxylate,
4% of trans-4-propylcyclohexyl trans,trans-4-butylcyclohexyl-cyclohexane-4'-carboxylate
3% of trans-4-pentylcyclohexyl trans,trans-4-butylcyclohexyl-cyclohexane-4'-carboxylate
6% of 4-(trans-4-pentylcyclohexyl)-2'-fluoro-4'-(trans-4-propylcyclohexyl)-biphenyl
4% of 4-trans-4-propylcyclohexyl-2'-fluoro-4'-(trans-4-propylcyclohexyl)-biphenyl,
3% of 4-(trans-4-pentylcyclohexyl)-2'-fluoro-4'-(trans-4-pentylcyclohexyl)-biphenyl,
6% of 4-(trans-4-pentylcyclohexyl)-4'-(trans-4-propylcyclohexyl)-biphenyl and
4% of 4-(trans-4-propylcyclohexyl)-4'-(trans-4-propylcyclohexyl)-biphenyl,
has a b.p. of 101° (extr.) and an HTP of +3.3.

EXAMPLE E

A liquid crystal phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-1-butyl-cis-4-(4'-octyloxybiphenyl-4-yl)cyclohexane, 14% of r-1-cyano-1-hexyl-cis-4-(4'-heptylbiphenyl-4-yl)cyclohexane,
6% of r-1-cyano-1-(4-pentylcyclohexyl)-cis-4-(4-pentylcyclohexyl)cyclohexane and
10% of 4-[3-chloro-4-octyloxybenzoyloxy]-4'-(2-chloro-3-methylbutyryloxy)-biphenyl
has a Sc* 78° $S_A$ 83° Ch 102° I and a spontaneous polarization Ps of 20 nC/cm².

EXAMPLE F

A liquid crystal phase consisting of
3% of 2-p-hexyloxyphenyl-5-heptylpyrimidine,
3% of 2-p-heptyloxyphenyl-5-heptylpyrimidine,
3% of 2-p-octyloxyphenyl-5-heptylpyrimidine,
3% of 2-p-nonyloxyphenyl-5-heptylpyrimidine,
7% of 2-p-hexyloxyphenyl-5-nonylpyrimidine,
23% of 2-p-nonyloxyphenyl-5-nonylpyrimidine,
28% of r-1-cyano-1-butyl-cis-4-(4'-octyloxybiphenyl-4-yl)cyclohexane,
14% of r-1-cyano-1-hexyl-cis-4-(4'-heptylbiphenyl-4-yl)cyclohexane,
6% of r-1-cyano-1-(4-pentylcyclohexyl)-cis-4-(4-pentylcyclohexyl)cyclohexane and
10% of 4-[3-cyano-4-octylbenzoyloxy]-4'-(2-chloro-3-methylbutyryloxy)-biphenyl
has Sc* 75° $S_A$ 78° Ch 98° I and a spontaneous polarization Ps of 18 nC/cm².

We claim:

1. A ferroelectric liquid crystal phase comprising at least two liquid crystal components, wherein at least one component is of the formula I

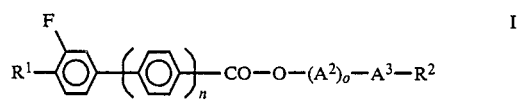

wherein
R¹ and R² each independently of one another is R, OR, OCOR, COOR or OCOOR,
R is straight-chain alkyl of 5 to 12 C atoms,
A² and A³ are each 1,4-phenylene, and
n and o are each independently 0 or 1.

2. In an electrooptical display element comprising a liquid crystalline dielectric, the improvement wherein the dielectric is a phase according to claim 1.

* * * * *